(12) United States Patent
Chen et al.

(10) Patent No.: US 6,930,209 B2
(45) Date of Patent: Aug. 16, 2005

(54) LIQUID PHASE OXIDATION OF CYCLOALKANE COMPOUND

(75) Inventors: Jenq-Renn Chen, Taipei (TW); Hsiao-Hui Yang, Taipei (TW); Chung-Ho Wu, Taipei (TW)

(73) Assignee: Chinese Petrochemical Development Co., Ltd. (TW)

( * ) Notice: Subject to any disclaimer, the term of this patent is extended or adjusted under 35 U.S.C. 154(b) by 14 days.

(21) Appl. No.: 10/442,508

(22) Filed: May 20, 2003

(65) Prior Publication Data

US 2004/0162445 A1 Aug. 19, 2004

(30) Foreign Application Priority Data

Feb. 19, 2003 (TW) ........................................ 92103368 A

(51) Int. Cl.$^7$ ........................... C07C 45/33; C07C 35/20
(52) U.S. Cl. ........................ 568/357; 568/375; 568/376; 568/821; 568/822; 568/836
(58) Field of Search ................................ 568/357, 375, 568/376, 821, 822, 836

(56) References Cited

U.S. PATENT DOCUMENTS

| | | | |
|---|---|---|---|
| 2,565,087 A | * | 8/1951 | Cosby et al. ............... 568/836 |
| 2,851,496 A | | 9/1958 | Cates, Jr. et al. ........... 260/586 |
| 3,870,760 A | * | 3/1975 | Tanaka et al. .............. 568/357 |
| 3,957,876 A | | 5/1976 | Rapoport et al. ........... 260/586 |
| 3,987,100 A | | 10/1976 | Barnette et al. ............ 260/586 |
| 4,326,084 A | * | 4/1982 | Druliner et al. ............ 502/167 |
| 4,658,056 A | | 4/1987 | Sipos ........................ 562/523 |
| 5,043,481 A | * | 8/1991 | Nedwick .................... 568/570 |
| 5,780,683 A | | 7/1998 | Greene et al. ............. 568/358 |
| 6,008,415 A | | 12/1999 | Greene et al. ............. 568/358 |
| 6,075,169 A | | 6/2000 | Rehfinger et al. .......... 568/358 |

FOREIGN PATENT DOCUMENTS

TW 150309 1/1991

* cited by examiner

*Primary Examiner*—Johann Richter
*Assistant Examiner*—Sikarl A. Witherspoon
(74) *Attorney, Agent, or Firm*—Peter F. Corless; John B. Alexander; Edwards & Angell, LLP

(57) ABSTRACT

A method for liquid phase oxidation of a cycloalkane compound is provided by which the cycloalkane compound intended to be oxidized mixes with water to form an azeotropic mixture, and then an oxygen enriched gas is introduced to perform an oxidation reaction. This method is particularly suitable for liquid phase oxidation of cyclohexane by using an oxygen enriched gas or pure oxygen, which not only enhances conversion rate and selectivity of the cyclohexane oxidation process but also improves process safety in the use of an oxygen enriched gas or pure oxygen for cyclohexane oxidation.

13 Claims, No Drawings

LIQUID PHASE OXIDATION OF CYCLOALKANE COMPOUND

FIELD OF THE INVENTION

The present invention relates to methods for oxidizing cycloalkane compounds in a liquid phase with the use of oxygen enriched gases, and more particularly, to a method for liquid phase oxidation of a cyclohexane compound in the use of a gas containing a high concentration of oxygen or pure oxygen.

BACKGROUND OF THE INVENTION

Liquid phase oxidation of cycloalkane compounds plays an important role in the petrochemical industries. Among various liquid phase oxidation reactions, oxidation of cyclohexane is a considerably important route to produce cyclohexanol, cyclohexanone and adipic acid, whereby cyclohexanol and cyclohexanone can further react to form caprolactam. Moreover, caprolactam can undergo decyclization and polymerization to produce Nylon 6, while adipic acid and hexylene diamine are condensed and polymerized to produce Nylon 66.

Currently, cyclohexane and phenol are used as raw materials for producing cyclohexanone and caprolactam. As preparation of cyclohexanone by using phenol added with hydrogen is relatively higher in cost, conventionally cyclohexane is used as a reactant and charged with air to be oxidized under high temperature and high pressure conditions. This oxidation reaction firstly forms a hexyl hydroperoxide as an intermediate which then decomposes to be cyclohexanone and cyclohexanol customarily referred to as KA oil, wherein cyclohexanol further needs to be dehydrogenated to form cyclohexanone, and cyclohexanone after undergoing amination is subject to the Beckmann rearrangement reaction to produce caprolactam with the use of sulfuric acid as a catalyst.

In general, conventionally oxidation of cyclohexane is performed at a temperature between 140° C. to 170° C. and under an air pressure of 5 to 25 bar or a higher pressure. This cyclohexane oxidation is carried out by air to produce a hexyl hydroperoxide (intermediate), cyclohexanol and cyclohexanone with or without using a catalyst. However, conversion rate of cyclohexane oxidation is not high, normally below 10%. For example, as reported in Taiwanese Patent Publication No. 150309, target products, cyclohexanone and cyclohexanol, from oxidation of cyclohexane are low oxidation state compounds and easily further react to form high oxidation state compounds. As a result, by such a conventional cyclohexane oxidation process, selectivity of cyclohexanone and cyclohexanol is not good, and the low conversion oxidation reaction would primarily reduce acids or other side products produced from over oxidation. Therefore, it is critical to control product selectivity in order to improve the conventional oxidation process; besides, improvement in conversion rate can help reduce load of product separation and increase unit space-time-yield, thereby enhancing reaction rate of the oxidation process.

Moreover, in the petrochemical industries, conversion rate and selectivity of the foregoing cyclohexane oxidation process can normally be improved by addition of catalysts. In a reaction of liquid phase oxidation of carbohydrates, it usually uses transition metal ions or complexes thereof as homogenous catalysts to enhance reaction rate. These transition metal ions can be $Co^{2+}$, $Cr^{2+}$, $Mn^{2+}$, $Cu^{2+}$, $Ni^{2+}$ and the like, wherein $Co^{2+}$ has the most preferable activity. For example, U.S. Pat. No. 3,987,100 discloses oxidation of cyclohexane performed by air with addition of $Co^{2+}$ and $Cr^{2+}$ as binary catalysts (0.1–5 ppm $Co^{2+}$ and 0.02–0.9 ppm $Cr^{2+}$). U.S. Pat. No. 4,658,056 teaches the use of a binary catalyst of combining bi[di(2-ethylhexyl)phosphoric acid] cobalt and cycloalkanoic acid chromium for performing oxidation with air under high temperature and high pressure conditions. In U.S. Pat. No. 2,851,496, cyclohexane oxidation is carried out with air at a reaction temperature of 160° C. and a reaction pressure of 160 psi, and products obtained from oxidation are allowed to contact with a sintered cobalt oxide fixed bed reactor at 70° C. for 15 minutes to improve conversion rate and selectivity of the cyclohexane oxidation reaction. Luna et al ("Cyclohexane Oxidation Using Transition Metal-Containing Aluminophosphates (MAPO-VFI)", *Journal of Molecular Catalysis*, vol. 117, pp. 405–411) propose the use of MAPO-VFI as a catalyst in the cyclohexane oxidation reaction, which can increase a ketone alcohol ratio to be 15.3; however, the reaction time for this oxidation reaction is longer than 24 hours, and an amount of catalyst as high as 1% is required, thereby not suitably applied to large scale production in the industry.

In another aspect, conversion rate and selectivity of cyclohexane oxidation can also be improved by modifying a gas-liquid contact way for an introduced gas. For example, in U.S. Pat. No. 3,957,876, a distilling tower reactor is used to allow fed cyclohexane to flow downwardly and effectively mix with upwardly moving air distributed in different layers, wherein each layer is provided with an oxygen removing layer used to maintain concentration of incompletely reacted oxygen below 4% from liquid space to vapor space in the distilling tower so as not to form explosive gaseous mixtures. U.S. Pat. No. 6,075,169 discloses the use of gas-liquid countercurrent to enhance mass transfer effect between air and liquid cyclohexane. However, these patents fail to effectively increase a ketone alcohol ratio for the cyclohexane oxidation process.

Besides, conversion rate and selectivity of the cyclohexane oxidation process can also be improved by introduction of an oxygen enriched gas (containing more than 21% oxygen) or pure oxygen. However, this method of using the oxygen enriched gas or pure oxygen may induce potential deflagration and thus is hardly applied to the industry. Deflagration is a type of burning reaction; mixtures of inflammable gases and oxidants such as oxygen are burned and lead to significant increase in temperature and pressure, which is customarily referred to as deflagration or explosion. Deflagration is induced by complete oxidation, instead of incomplete or partial oxidation, incurred in the oxidation process, which may render serious risks as the reaction exceeds explosion limits, whereby the pressure would instantly raise and possibly causes the reactor to explode.

U.S. Pat. Nos. 5,780,683 and 6,008,415 propose the use of a special liquid phase oxidation reactor in which an oxygen enriched gas or pure oxygen is charged and used for oxidation of cyclohexane; special downwardly stirring blades are adopted to mix cyclohexane and the oxygen enriched gas, and an enclosure is used to effectively block and consume oxygen, allowing incompletely reacted oxygen in a small amount to be deactivated by nitrogen when passing from liquid space to vapor space. Compared to conventional oxidation in the use of air, with the same cyclohexane conversion of 4%, the above oxidation process by using the oxygen enriched gas or pure oxygen reduces the reaction temperature from 160° C. to 149° C. and reduces reaction residence time from 36 minutes to 8 minutes, as well as increases space-time-yield from 0.45 gmol/hr·L to 1.85 gmol/hr·L and increases a ratio of cyclohexanone to cyclohexanol from 0.48 to 0.77. Therefore, in compliance with safety requirements, the cyclohexane oxidation process can be performed under the same reaction conditions but with increased oxygen concentration of the oxygen enriched gas to improve yield and productivity thereof. However, Williams et al. ("Developing Safe Oxygen-Based Commercial Liquid-Phase Oxidation Reactors" *AlChE Annual Meeting*, Miami, Fla., 1998) has reported that cyclohexane oxidation performed by using oxygen enriched gases or pure oxygen may exceed explosion limits of cyclohexane and lead to potential risks e.g. deflagration as bubbles of oxygen enriched gases or pure oxygen contain cyclohexane vapor; this should be of significant concerns in respect of large scale production in the industry. In addition, controls of oxygen dispersion and stirring play an important role in this oxidation process; if stirring is not effective, bubbles in liquid phase would coagulate to form partial and potentially explosive vapor space, such that the oxidation process needs to be carefully operated in practice.

SUMMARY OF THE INVENTION

An objective of the present invention is to provide a method for liquid phase oxidation of a cycloalkane compound to improve reaction yield and conversion rate and ensure safe operation of the oxidation reaction.

The method according to the invention is implemented by firstly contacting a cycloalkane compound intended to be oxidized with water to form an azeotropic mixture, and then introducing an oxygen enriched gas to perform oxidation. In respect of cyclohexane oxidation, the use of an oxygen enriched gas (even pure oxygen) for oxidation can improve process yield and a ketone alcohol ratio even without using catalysts, and can also reduce the reaction temperature and discharge and treatment of tail gas. Therefore, when the liquid phase oxidation method according to the invention is applied to cyclohexane oxidation, it is not necessary to add nitrogen for deactivation but can eliminate the risk of potential deflagration with the use of the oxygen enriched gas and also increase the process yield and ketone alcohol ratio.

DETAILED DESCRIPTION OF THE PREFERRED EMBODIMENTS

The present inventors have researched and found that, cyclohexane and water mix to form a positive pressure azeotropic mixture; in other words, due to azeotropy, a vapor pressure of the mixture is higher than that of each single component. The raised vapor pressure of the mixture contains a large amount of water vapor that can replace nitrogen to be used for deactivation during oxidation. Therefore, it is not necessary to introduce nitrogen for deactivation in a cyclohexane oxidation process using an oxygen enriched gas or pure oxygen. The method according to the invention is to add water to cyclohexane to form a positive pressure azeotropic mixture; the large amount of water vapor in this azeotropic mixture can replace nitrogen to be used for deactivation, so as to maintain gas concentration within a safety range in the reaction. As a result, potential deflagration can be effectively prevented even in the use of pure oxygen for performing cyclohexane oxidation.

Moreover, the positive pressure azeotropic mixture formed from cyclohexane and water is controllable by temperature, but the pressure of the azeotropic mixture is not of significant relevance to stirring. As such, in the case of using an oxygen enriched gas or pure oxygen for performing cyclohexane oxidation, if stirring is accidentally stopped, it only needs to control the reaction temperature to prevent excess oxygen concentration and deflagration, and still provides sufficient time to take proper actions such as quickly adding nitrogen for dilution to eliminate the occurrence of deflagration and ensure safe operation for the reaction. Therefore, the liquid phase oxidation method according to the invention applied to cyclohexane oxidation can use pure oxygen for oxidation to improve conversion rate and selectivity of the oxidation reaction and obtain a higher ketone alcohol ratio as well as reduce the load of dehydrogenation of cyclohexanol into cyclohexanone and assure safe operation and productivity for the overall process, thereby possessing considerably high economic efficiency.

In another aspect, water added to cyclohexane oxidation would not affect performance of the oxidation reaction. For example, U.S. Pat. No. 2,565,087 discloses an oxidation process for cycloaliphatic compounds in which 10% to 30% water is added to cyclohexane oxidized by air and can effectively inhibit production of by-products such as ester. However, this patent does not teach the formation of a positive pressure azeotropic mixture from cyclohexane and water, which positive pressure azeotropic mixture contains a large amount of water vapor and thereby replaces nitrogen for deactivation in the oxidation process that can thus use oxygen enriched gases or pure oxidation without safety concerns. Theoretically, the amount of water added to the cyclohexane oxidation reaction would not affect reaction performance; however, the water added may occupy effective reaction volume and thus reduces yield of unit volume and time. As such, when the liquid phase oxidation method according to the invention is used in cyclohexane oxidation, water is not necessarily added to the oxidation process in an amount of 10% to 30% as disclosed in U.S. Pat. No. 2,565,087; instead, the amount of water added is merely required to allow a partial pressure of water of the azeotropic mixture in vapor space to sufficiently deactivate pure oxygen used in the process. In general, an accurate amount of water to be added depends on a practical operation temperature and explosion test results. Under suitable conditions, the less amount the added water, the better the production yield is; for example, the production yield may raise up to two times or more than that through the use of air.

With cyclohexane oxidation being performed by the liquid phase oxidation method according to the invention, preferably 0.01% to 50% water, more preferably 0.1% to 30% water, is added to cyclohexane to form the positive pressure azeotropic mixture under a temperature condition of 100° C. to 200° C., preferably 140° C. to 170° C. Then, the oxygen enriched gas particularly having the oxygen concentration of 30% to 100%, or pure oxygen beyond the explosive ranges, is introduced with a feed pressure thereof higher than a vapor pressure of the positive pressure azeotropic mixture by 0.001 to 10 bar, preferably 0.1 to 2 bar, to perform the oxidation reaction. The feed pressure of the oxygen enriched gas can be adjusted according to the reaction temperature and the amount of water being added; and the reaction gas can be fed in a continuous one-in-one-out manner or is fed in a closed manner only when gas insufficiency is incurred. In the use of pure oxygen for performing the oxidation reaction, the closed manner of gas feeding when insufficiency is incurred can reduce discharge and treatment of reaction waste oases, which is environmentally friendly and saves costs for discharge and treatment of reaction waste gases to compensate the costs of using pure oxygen, thereby in compliance with the cost concern.

The liquid phase oxidation method according to the invention is suitably applied to a continuous or batch operation mode, preferably the continuous operation mode. Moreover, a reactor used in the method according to the invention can be a single or a series of stirring tanks or bubble columns, and usually the series of stirring tanks are preferred. Therefore, in concern of equipment costs, by using the method according to the invention, it is not necessary to utilize additional equipment but can overcome the problem of inducing the risk of potential deflagration from the use of the oxygen enriched gas for the oxidation reaction as well as production yield and process safety can be increased.

The method according to the invention can be performed free of using a catalyst or with suitable catalysts. These suitable catalysts can be selected by persons skilled in the art according the types of carbohydrates and reaction systems to be used.

Moreover, besides cyclohexane oxidation, the liquid phase oxidation method according to the invention can also be suitably applied to a process for oxidizing other cycloalkane compounds which can azeotropically mix with water, particularly cycloalkane compounds having 4 to 14 carbon atoms, such as cyclopentane, cycloheptane, cyclooctane, cyclononene, cyclodecane, and so on. However, when the method according to the invention is used in oxidation of carbohydrates, it is required that the fed pure oxygen needs to be beyond the explosive ranges, whose precise amount should be determined according to practical measurement such as the method disclosed by J. R. Chen and K. Liu ("A Simple Apparatus for Flammability at Elevated Pressures", 2001 *Asia-Pacific Symposium on Safety,* Kyoto, Japan, November 2001).

EXAMPLES

Example 1

In a high temperature and high pressure reactor such as autoclave, 1500 ml of a mixture of cyclohexane and water (volume ratio is 95:5, weight ratio is 93.7:6.3) is added, and upon the temperature reaching 165° C., pure oxygen having a feed pressure higher than a vapor pressure of the mixture by 1 bar is introduced in a closed manner when gas insufficiency is incurred, and stirred to perform the oxidation reaction. The space-time-yield of cyclohexanone, total usable yield for cyclohexanone, cyclohexanol and cyclohexyl hydroperoxides, and a ratio of cyclohexanone to cyclohexanol are recorded as shown in Table 1 below:

TABLE 1

| Reaction time (hr) | Space-time-yield of cyclohexanone (gmol/L · hr) | Total usable yield (gmol/L · hr) | Ratio of cyclohexanone to cyclohexanol |
|---|---|---|---|
| 1 | 0.0706 | 0.203 | 1.44 |
| 1.5 | 0.0544 | 0.171 | 0.622 |
| 2 | 0.0342 | 0.110 | 0.503 |

Example 2

In an autoclave, 1500 ml of a mixture of cyclohexane and water (volume ratio is 95:5, weight ratio is 93.7:6.3) is added, and upon the temperature reaching 160° C., pure oxygen having a feed pressure higher than a vapor pressure of the mixture by 1 bar is introduced in a closed manner when gas insufficiency is incurred, and stirred to perform the oxidation reaction. The space-time-yield of cyclohexanone, total usable yield for cyclohexanone, cyclohexanol and cyclohexyl hydroperoxides, and a ratio of cyclohexanone to cyclohexanol are recorded as shown in Table 2 below:

TABLE 2

| Reaction time (hr) | Space-time-yield of cyclohexanone (gmol/L · hr) | Total usable yield (gmol/L · hr) | Ratio of cyclohexanone to cyclohexanol |
|---|---|---|---|
| 1 | 0.0430 | 0.131 | 3.27 |
| 1.5 | 0.0468 | 0.130 | 1.35 |
| 2 | 0.0411 | 0.127 | 0.819 |

Example 3

In an autoclave, 1500 ml of a mixture of cyclohexane and water (volume ratio is 95:5, weight ratio is 93.7:6.3) is added, and upon the temperature reaching 155° C., pure oxygen having a feed pressure higher than a vapor pressure of the mixture by 1 bar is introduced in a closed manner when gas insufficiency is incurred, and stirred to perform the oxidation reaction. The space-time-yield of cyclohexanone, total usable yield for cyclohexanone, cyclohexanol and cyclohexyl hydroperoxides, and a ratio of cyclohexanone to cyclohexanol are recorded as shown in Table 3 below:

TABLE 3

| Reaction time (hr) | Space-time-yield of cyclohexanone (gmol/L · hr) | Total usable yield (gmol/L · hr) | Ratio of cyclohexanone to cyclohexanol |
|---|---|---|---|
| 1 | 0.0124 | 0.0441 | 1.89 |
| 1.5 | 0.0152 | 0.0513 | 3.63 |
| 2 | 0.0240 | 0.0740 | 3.01 |

Example 4

In an autoclave, 1500 ml of a mixture of cyclohexane and water (volume ratio is 75:25, weight ratio is 70.3:29.7) is added, and upon the temperature reaching 165° C., pure oxygen having a feed pressure higher than a vapor pressure of the mixture by 1 bar is introduced in a closed manner when gas insufficiency is incurred, and stirred to perform the oxidation reaction. The space-time-yield of cyclohexanone, total usable yield for cyclohexanone, cyclohexanol and cyclohexyl hydroperoxides, and a ratio of cyclohexanone to cyclohexanol are recorded as shown in Table 4 below:

TABLE 4

| Reaction time (hr) | Space-time-yield of cyclohexanone (gmol/L · hr) | Total usable yield (gmol/L · hr) | Ratio of cyclohexanone to cyclohexanol |
|---|---|---|---|
| 1 | 0.0166 | 0.0688 | 0.999 |
| 1.5 | 0.0217 | 0.0777 | 0.815 |
| 2 | 0.0284 | 0.0722 | 0.827 |

Example 5

In an autoclave, 1500 ml of a mixture of cyclohexane and water (volume ratio is 75:25, weight ratio is 70.3:29.7) is added, and upon the temperature reaching 160° C., pure oxygen having a feed pressure higher than a vapor pressure of the mixture by 1 bar is introduced in a closed manner when gas insufficiency is incurred, and stirred to perform the oxidation reaction. The space-time-yield of cyclohexanone, total usable yield for cyclohexanone, cyclohexanol and cyclohexyl hydroperoxides, and a ratio of cyclohexanone to cyclohexanol are recorded as shown in Table 5 below:

TABLE 5

| Reaction time (hr) | Space-time-yield of cyclohexanone (gmol/L · hr) | Total usable yield (gmol/L · hr) | Ratio of cyclohexanone to cyclohexanol |
|---|---|---|---|
| 1 | 0.0072 | 0.0377 | 1.48 |
| 1.5 | 0.0135 | 0.0530 | 1.49 |
| 2 | 0.0238 | 0.0648 | 1.19 |

Comparative Example 1

In an autoclave, 600 ml of cyclohexane is added, and upon the temperature reaching 165° C., air is introduced in a continuous one-in-one-out manner to read a pressure of 12 bar and stirred to perform the oxidation reaction. The space-time-yield of cyclohexanone, total usable yield for cyclohexanone, cyclohexanol and cyclohexyl hydroperoxides, and a ratio of cyclohexanone to cyclohexanol are recorded as shown in Table 6 below:

TABLE 6

| Reaction time (hr) | Space-time-yield of cyclohexanone (gmol/L · hr) | Total usable yield (gmol/L · hr) | Ratio of cyclohexanone to cyclohexanol |
|---|---|---|---|
| 1 | 0.0338 | 0.101 | 0.761 |
| 1.5 | 0.0355 | 0.104 | 0.633 |
| 2 | 0.0310 | 0.089 | 0.612 |

In conclusion, when the liquid phase oxidation method according to the invention is applied to cyclohexane oxidation, cyclohexane mixes with water to form a positive pressure azeotropic mixture, which can overcome the problem of inducing the risk of potential deflagration in the use of an oxygen enriched gas or pure oxygen for performing the oxidation reaction. On the other hand, compared to a conventional oxidation process using air, under the same temperature condition, better space-time-yield of cyclohexanone and total usage yield are obtained by the method according to the invention. Moreover, the method according to the invention is suitably applied to the oxidation process using pure oxygen to improve the ratio of cyclohexanone to cyclohexanol and effectively enhance conversion rate and selectivity of the oxidation process.

What is claimed is:

1. A method for liquid phase oxidation of a cycloalkane compound, comprising the steps of:
    forming an azeotropic mixture of the cycloalkane compound and water; and
    introducing an oxygen enriched gas into the azeotropic mixture to perform an oxidation reaction, wherein the oxygen enriched gas is introduced with a feed pressure thereof higher than a vapor pressure of the azeotropic mixture by 0.001 to 10 bar.

2. The method of claim 1, wherein the cycloalkane compound is selected from the group consisting of cyclopentane, cyclohexane, cycloheptane, cyclooctane, cyclononane, and cyclodecane.

3. The method of claim 2, wherein the cycloalkane compound is cyclohexane.

4. The method of claim 3, wherein the cyclohexane mixes with 0.01–50% wt % water to form the azeotropic mixture under a temperature condition of 100° C. to 200° C.

5. The method of claim 4, wherein the cyclohexane mixes with 0.1–30 wt % water to form the azeotropic mixture under a temperature condition of 140° C. to 170° C.

6. The method of claim 1, wherein the oxygen enriched gas is introduced with a feed pressure thereof higher than the vapor pressure of the azeotropic mixture by 0.1 to 2 bar.

7. The method of claim 6, wherein oxygen concentration of the oxygen enriched gas is 30% to 100%.

8. The method of claim 7, wherein the oxygen concentration of the oxygen enriched gas is 90% to 100%.

9. The method of claim 8, wherein the oxygen enriched gas is fed in a close manner when gas insufficiency is incurred.

10. The method of claim 9, wherein the oxidation reaction is performed in a series of stirring tanks.

11. The method of claim 10, wherein the oxidation reaction is operated in a continuous mode.

12. The method of claim 1, wherein the oxidation reaction is performed in a condition of using a catalyst.

13. The method of claim 1, wherein the oxidation reaction is performed in a condition free of using a catalyst.

* * * * *